United States Patent [19]

Okawa

[11] Patent Number: 5,614,640
[45] Date of Patent: Mar. 25, 1997

[54] EPOXY FUNCTIONAL SILOXANES

[75] Inventor: Tadashi Okawa, Chiba Prefecture, Japan

[73] Assignee: Dow Corning Toray Silicone Co., Ltd., Tokyo, Japan

[21] Appl. No.: 620,697

[22] Filed: Mar. 21, 1996

[30]  Foreign Application Priority Data

Mar. 22, 1995 [JP] Japan .................................. 7-090190

[51] Int. Cl.$^6$ .............................. C07F 7/08; C07D 303/02
[52] U.S. Cl. ................................................ 549/215
[58] Field of Search ............................................ 549/215

[56]  References Cited

U.S. PATENT DOCUMENTS 4,788,268  11/1988  Lau et al. ............................ 549/215 X
5,420,323   5/1995  Jung et al. .......................... 549/215 X
5,512,640   4/1996  Osawa et al. ....................... 549/215 X

FOREIGN PATENT DOCUMENTS 2008848  8/1990  Canada .

*Primary Examiner*—Paul F. Shaver
*Attorney, Agent, or Firm*—Timothy J. Troy

[57]  ABSTRACT

This invention relates to novel alicyclic epoxy-functional siloxanes. The invention also relates to a method for the preparation of these epoxy-functional siloxanes. The epoxy functional siloxanes of this invention can be added to photocurable compositions which when exposed to ultraviolet radiation will yield a highly releasing, very printable/writable, and highly water-repellent cured film.

20 Claims, No Drawings

EPOXY FUNCTIONAL SILOXANES

BACKGROUND OF THE INVENTION

This invention relates to novel alicyclic epoxy-functional siloxanes. The invention also relates to a method for the preparation of these epoxy-functional siloxanes.

Graft copolymers carrying pendant epoxy groups can be prepared by the copolymerization of a radical-polymerizing monomer with a monomer that bears both an epoxy group and a radical-polymerizing functional group. However, since the epoxy group in the prior-art epoxy-functional graft copolymers is the glycidoxy group, these copolymers suffer from the problem of a low ring-opening and crosslinking reactivity under the action of electrophilic reagents such as, for example, acids. This has led to a search for graft copolymers that would contain the highly reactive alicyclic epoxy group.

Alicyclic epoxy-functional siloxanes are known, for example, in the form of the compound

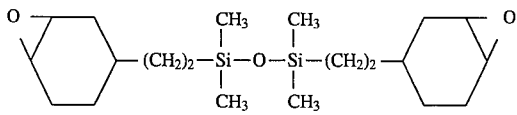

which is disclosed in Japanese Patent Application Laid-Open No. 3-20374 (20,374/1991). However, siloxanes bearing both alicyclic epoxy groups and radical-polymerizing functional groups, which would be able to function as a precursor for epoxy-functional graft copolymers, are heretofore unknown.

SUMMARY OF THE INVENTION

This invention relates to novel alicyclic epoxy-functional siloxanes and to a method for the preparation of these epoxy-functional siloxanes.

It is an object of the present invention to introduce novel alicyclic epoxy-functional siloxanes.

Another object of the invention is to introduce a method for the preparation of these novel epoxy-functional siloxanes.

DETAILED DESCRIPTION OF THE INVENTION

The present invention relates to alicyclic epoxy-functional siloxanes having the formula

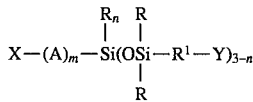

wherein X is a group selected from the group consisting of acryloxy, methacryloxy, and vinylphenyl, Y is an alicyclic epoxy group, each R is independently selected from monovalent hydrocarbon groups free of aliphatic unsaturation, $R^1$ is a divalent hydrocarbon group having at least 2 carbon atoms, A is selected from $R^1$ or a group having the formula $-R^2-O-R^2-$ wherein $R^2$ is a divalent hydrocarbon group, m has an average value of 0 or 1, and n has an average value of 0, 1, or 2.

The group X in the above formula is a group selected from the group consisting of acryloxy, methacryloxy, and vinylphenyl groups. The vinylphenyl group is exemplified by groups such as 4-vinylphenyl, 3-vinylphenyl, or 2-vinylphenyl. The methacryloxy group is preferred. The group X functions as the radical-polymerizing functional group on the siloxanes of the present invention.

The group Y is an alicyclic epoxy group, examples of which include 3,4-epoxycyclohexyl or 4-methyl-3,4-epoxycyclohexyl. Each R is independently selected from monovalent hydrocarbon groups which are free of aliphatically unsaturated bonds. Examples thereof are alkyl groups such as methyl, ethyl, butyl, pentyl, or hexyl, aryl groups such as phenyl, tolyl, or xylyl, and aralkyl groups such as benzyl, or phenethyl. The group $R^1$ is a divalent hydrocarbon group having 2 or more carbon atoms and is exemplified by alkylene groups such as ethylene, propylene, butylene, or hexylene, and by arylene groups such as phenylene. The group A is $R^1$ as defined above or a group having the formula $-R^2-O-R^2-$ wherein $R^2$ is a divalent hydrocarbon group. The group $R^2$ is exemplified by alkylene or arylene groups as delineated above. The group A is preferably selected from ethylene, propylene, butylene, hexylene, or ethyleneoxypropylene. The subscript m has an average value of 0 or 1. The subscript m is preferably 0 when X is vinylphenyl. The subscript n has an average value of 0, 1, or 2. The epoxy-functional siloxanes according to the present invention will have 3 alicyclic epoxy groups when n is 0, 2 alicyclic epoxy groups when n is 1, and 1 alicyclic epoxy group when n is 2.

The alicyclic epoxy-functional siloxanes according to the present invention are exemplified by compounds having the formula

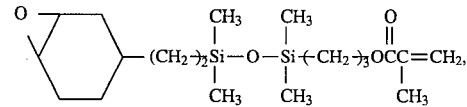

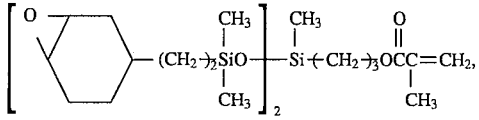

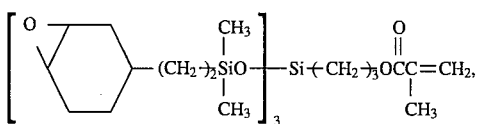

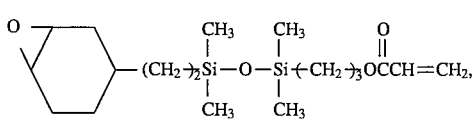

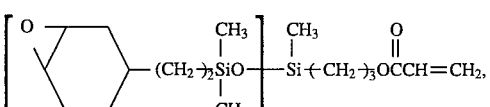

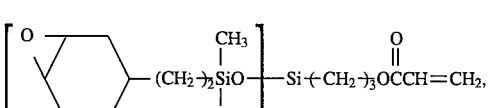

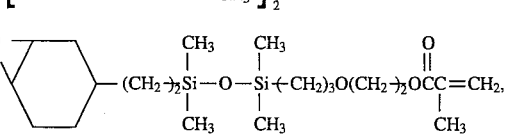

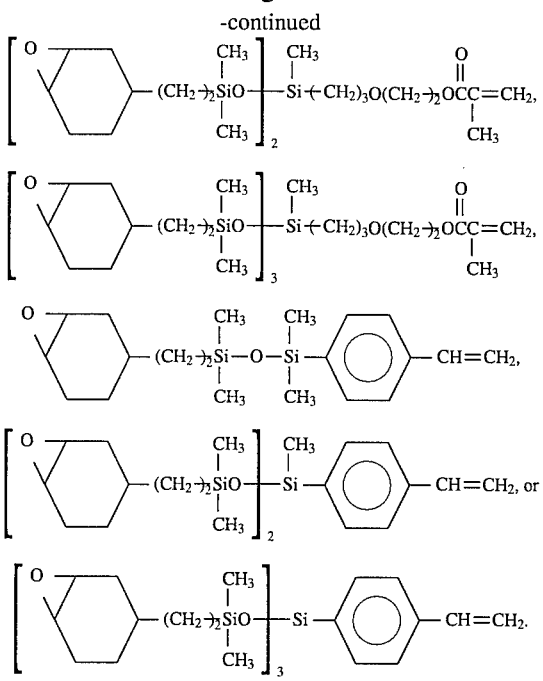

The present invention also relates to a method for the preparation of alicyclic epoxy-functional siloxanes, wherein the method comprises the step of (I) reacting a mixture of: (A) an organohydrogensiloxane having the formula

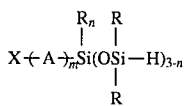

wherein X is a group selected from the group consisting of acryloxy, methacryloxy, and vinylphenyl, each R is independently selected from monovalent hydrocarbon groups free of aliphatic unsaturation, A is selected from a divalent hydrocarbon group having at least 2 carbon atoms or a group having the formula $-R^2-O-R^2-$ wherein $R^2$ is a divalent hydrocarbon group, m is 0 or 1, and n is an integer from 0 to 2, and (B) an aliphatically unsaturated alicyclic epoxy compound having the general formula Z-Y wherein Z is a monovalent hydrocarbon group having an aliphatically unsaturated bond and Y is an alicyclic epoxy group in the presence of (C) a hydrosilylation reaction catalyst.

X, R, $R^2$, A, m and n in the preceding formula for the organohydrogensiloxane (A) are defined as above. This organohydrogensiloxane can be prepared by well-known methods. For example, it is disclosed in U.S. Pat. No. 3,398,017 that an organohydrogensiloxane having the formula $CH_2=C(CH_3)COO(CH_2)_3Si[OSi(CH_3)_2H]_3$ can be prepared by the dropwise addition of a silane having the formula $CH_2=C(CH_3)COO(CH_2)_3Si(OCH_3)_3$ and the silane $H(CH_3)_2SiCl$ into a solvent containing a mixture of water and ether. In addition, the organohydrogensiloxane can also be prepared by hydrolyzing a chlorosilane having a radical-polymerizing functional group in the presence of 1,1,3,3-tetramethyldisiloxane or by hydrolyzing a chlorosilane having a radical-polymerizing functional group to a silanol and then reacting this silanol with a diorganochlorosilane. In order to inhibit silanol group condensation, these procedures are preferably run using an amine, such as triethylamine or pyridine, as an acceptor for the evolved hydrogen chloride.

The group Z in the above formula for the aliphatically unsaturated alicyclic epoxy compound (B) is a monovalent hydrocarbon group containing an aliphatically unsaturated bond. This group Z is exemplified by groups such as vinyl, allyl, butenyl, and hexenyl, and vinyl is preferred. The group Y is an alicyclic epoxy group as described hereinabove and 3,4-epoxycyclohexyl is preferred.

The hydrosilylation reaction catalyst is exemplified by the complex catalysts of the transition metals of Group VIII of the Periodic Table. Among these, platinum catalysts are particularly effective, and platinum compounds such as chloroplatinic acid, alcohol solutions of chloroplatinic acid, platinum-olefin complexes, or platinum/vinylsiloxane complexes are preferred.

In order to prevent the reaction of component (A) with itself, the preferred method for reacting components (A) and (B) comprises preliminarily mixing the hydrosilylation reaction catalyst (C) with component (B) and thereafter gradually adding component (A) dropwise to this mixture. With regard to the proportions for components (A) and (B), the ratio of equivalents of aliphatically unsaturated bonds from component (B) to equivalents of SiH in component (A) is preferably at least 1.0, more preferably 1.1 to 2.0, and most preferably 1.2 to 1.5. While this reaction is preferably run in a suitable solvent, it may also be run in the absence of solvent. Suitable solvents include aromatics such as benzene, toluene, and xylene, aliphatics such as hexane and heptane, ethers such as tetrahydrofuran and diethyl ether, ketones such as acetone and methyl ethyl ketone, esters such as ethyl acetate and butyl acetate, chlorohydrocarbons such as carbon tetrachloride, trichloroethane, and chloroform, dimethylformamide, or dimethyl sulfoxide. The reaction can be run at room temperature, but is ordinarily preferably run at 50° C to 200° C based on reaction rate considerations. The reaction solution can be analyzed during the reaction by gas chromatography (GLC) or infrared spectrochemical analysis (IR), and completion of the reaction can be ascertained by the disappearance of the peak(s) for the organohydrogensiloxane (A). After completion of the reaction, the alicyclic epoxy-functional siloxane according to the present invention can be recovered by removal of the unreacted component (B) and low boilers, such as the solvent, by a method such as distillation at reduced pressure. The alicyclic epoxy-functional siloxane thus obtained is preferably subjected to additional purification by distillation.

Since the epoxy-functional siloxanes according to the present invention contain both an alicyclic epoxy group and a radical-polymerizing functional group within its molecule, it can be easily copolymerized with additional radical-polymerizing monomers to give an allcyclic epoxy-functional, silicone-grafted copolymer. The resulting graft copolymer, because it contains the highly reactive alicyclic epoxy group, will readily undergo ring-opening and crosslinking and thus can be deployed as a thermosetting polymer. In the case, for example, of the silicone-grafted copolymer afforded by the copolymerization of alicyclic epoxy-functional siloxane of the present invention with a radical-polymerizing monomer such as an acrylate monomer which is exemplified by alkyl acrylates such as methyl acrylate, ethyl acrylate, or butyl acrylate and a silicone macromonomer such as a compound having the formula

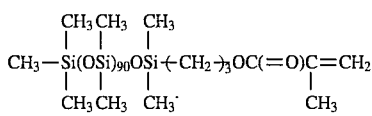

the addition of a photocuring catalyst to this copolymer followed by exposure to ultraviolet radiation will yield a highly releasing, very printable/writable, and highly water-repellent cured film. Preferably the photocuring catalyst is an onium salt. Preferred onium salts for use in the radiation curable compositions of this invention are diaryliodonium salts such as bis(dodecylphenyl)iodonium hexafluoroarsenate or bis(dodecylphenyl)iodonium hexafluoroantimonate.

The invention will be explained in greater detail below through working examples, in which parts denotes weight parts.

EXAMPLE 1

The following were introduced into a 1-Liter flask equipped with a stirrer, thermometer, condenser, and dropping funnel: 73.7 grams of 1,1,3,3-tetramethyldisiloxane, 18 grams of ice, 100 grams of water, and 50 grams of concentrated hydrochloric acid. Then 215.7 grams of methacryloxypropyldimethylchlorosilane was then added dropwise to this mixture while it was cooling on an ice water bath so as to keep the reaction temperature from exceeding 10° C. After completion of the addition, the flask was allowed to stand and the aqueous layer was separated off. The resulting organic layer was washed twice with water. The organic layer was then washed twice with a 5% aqueous sodium bicarbonate solution and thereafter washed an additional two times with water. The organic layer freed of the aqueous layer was dried over sodium sulfate, and the sodium sulfate was filtered off. 0.6 g of phenothiazine was added, and distillation in vacuum yielded 198 g of a fraction at 71° C–80° C/1 mmHg. Analysis of this fraction by nuclear magnetic resonance analysis (NMR) and infrared spectrochemical analysis (IR) confirmed it to be the disiloxane with the formula given below. This disiloxane was 99% pure by gas chromatography (GLC).

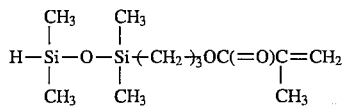

EXAMPLE 2

About 17.2 g 4-vinylcyclohexene oxide and 50 mL hexane were placed in a 200-mL flask equipped with a stirrer, thermometer, condenser, and addition funnel. This was followed by azeotropic drying with the application of heat for 10 minutes. After drying, the flask was cooled back to room temperature, and 0.06 g phenothiazine and 4.8 microliters platinum/vinylsiloxane complex (platinum metal concentration=12.4 weight%, prepared from chloroplatinic acid and 1,3-divinyltetramethyldisiloxane) were introduced. The flask was then heated to 70° C and 30 g of the disiloxane synthesized in Example 1 was added dropwise. The reaction was then stirred at 70° C for an additional 30 minutes after the completion of this addition, whereupon analysis of the reaction solution by GLC indicated that the peak for the starting disiloxane had disappeared and thereby confirmed completion of the reaction. The solvent and unreacted 4-vinylcyclohexene oxide were then distilled from the reaction solution by heating under reduced pressure to give 43.1 g of a residue. Analysis of this residue by NMR and IR confirmed it to be an alicyclic epoxy-functional siloxane having the formula given below. This siloxane was 98.0% pure by GLC.

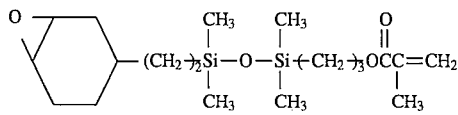

EXAMPLE 3

About 150 parts toluene was placed in a 100-mL flask equipped with a stirrer, thermometer, condenser, and nitrogen feed tube and bubbled with nitrogen for 30 minutes to remove the dissolved oxygen. To this flask were then added 30 parts butyl acrylate, 40 parts of the siloxane synthesized in Example 2, 30 parts of a silicone macromonomer having the average formula

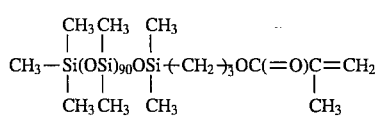

and 2 parts azobisisobutyronitrile. Nitrogen was then bubbled through the flask for another 30 minutes. Stirring the resulting mixture under nitrogen at 60° C for 24 hours yielded a toluene solution of an alicyclic epoxy-functional silicone-grafted polybutyl acrylate. The toluene and unreacted butyl acrylate were eliminated from the toluene solution by heating at reduced pressure to afford the alicyclic epoxy-functional silicone-grafted polybutyl acrylate as a semisolid. Next, 2 parts an onium salt curing catalyst (GE9130C from the General Electric Company) was added to 100 parts of this alicyclic epoxy-functional silicone-grafted polybutyl acrylate, and the resulting mixture was then dissolved in n-hexane to give a solids concentration of 7 weight%. This solution was coated on the polyethylene surface of polyethylene-coated paper using a bar coater to give a coating weight for the solids of 0.5 g/m². Curing was then effected by irradiating (130 mJ/cm²) the coated surface with an ultraviolet irradiator that contained a high-pressure mercury lamp. A commercial pressure-sensitive tape with a width of 38 mm (31B from Nitto Denko Kabushiki Kaisha) was pressed onto the treated polyethylene surface using one back-and-forth excursion with a tape roller (weight=2 kg). The assembly was then held for 20 hours at 70° C with a load of 20 g/cm² on the pressure-sensitive tape. The load was removed after this holding period and the assembly was allowed to cool for 2 hours. The pressure-sensitive tape was peeled off using a Tensilon at a rate of 300 mm/minute and an angle of 180° and the force (g/38 mm) required for peeling was measured. The result was 15 g/38 mm. After peeling, the pressure-sensitive tape was then folded in half in order to inspect the ability of the two halves to adhere to each other. Residual adhesion was observed, although somewhat inferior to the adhesion by the fresh tape. When characters were written on the polyethylene surface using a commercial oil-based ink pen, the characters could be written although crawling was observed. These results confirmed that a highly releasing, very writable film had been formed.

Comparison Example 1

For purposes of comparison, a glycidoxy-functional, silicone-grafted polybutyl acrylate was prepared using the above-described procedure from 47 parts butyl acrylate, 30 parts of the silicone macromonomer of Example 3, and 23 parts of glycidyl methacrylate (the glycidyl methacrylate was used in place of the alicyclic epoxy-functional siloxane whose synthesis is described in Example 2). About 2 parts of the above-described onium salt curing catalyst was added to 100 parts of this glycidoxy-functional silicone-grafted polybutyl acrylate, and the resulting mixture was then dissolved in n-hexane to give a solids concentration of 7 weight%. Using this solution the polyethylene surface of polyethylene-coated paper was treated as above. After the exposure to ultraviolet radiation, the polyethylene surface became blurred and cloudy when forcefully rubbed with a finger. This confirmed that film formation had not occurred.

That which is claimed is:

1. An alicyclic epoxy-functional siloxane compound having the formula

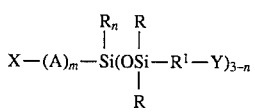

wherein X is a group selected from the group consisting of acryloxy, methacryloxy, and vinylphenyl, Y is an alicyclic epoxy group, each R is independently selected from monovalent hydrocarbon groups free of aliphatic unsaturation, $R^1$ is a divalent hydrocarbon group having at least 2 carbon atoms, A is selected from $R^1$ or a group having the formula $-R^2-O-R^2-$ wherein $R^2$ is a divalent hydrocarbon group, m has an average value of 0 or 1, and n has an average value 0, 1, or 2.

2. A compound according to claim 1, wherein the vinylphenyl group is selected from 4-vinylphenyl, 3-vinylphenyl, or 2-vinylphenyl.

3. A compound according to claim 1, wherein X is a methacryloxy group.

4. A compound according to claim 1, wherein Y is selected from 3,4-epoxycyclohexyl or 4-methyl-3,4-epoxycyclohexyl.

5. A compound according to claim 1, wherein R is selected from methyl or phenyl.

6. A compound according to claim 1, wherein $R^1$ is selected from ethylene, propylene, butylene, hexylene, or phenylene.

7. A compound according to claim 1, wherein A is selected from ethylene, propylene, butylene, hexylene, or ethyleneoxypropylene.

8. A compound according to claim 1, wherein the epoxy-functional siloxane compound is selected from

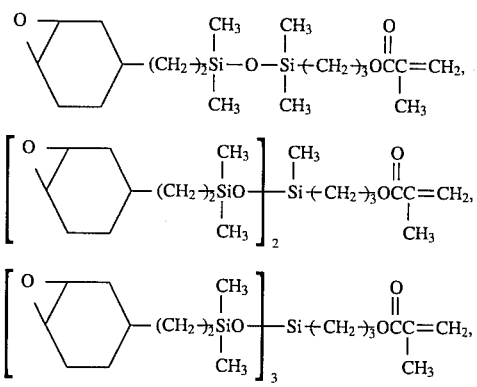

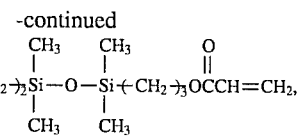

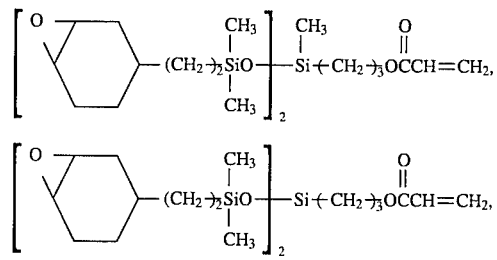

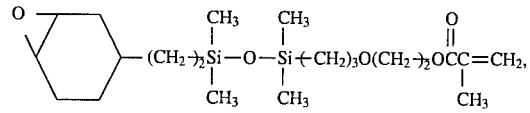

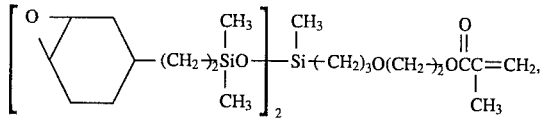

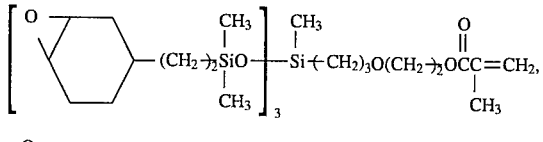

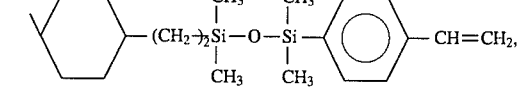

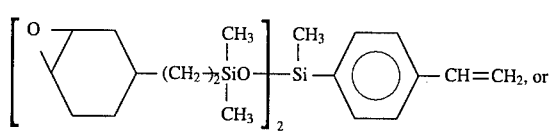

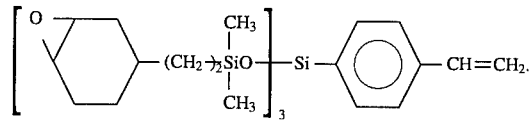

9. A method for the preparation of alicyclic epoxy-functional siloxanes, wherein the method comprises the step of (I) reacting a mixture of:

(A) an organohydrogensiloxane having the formula

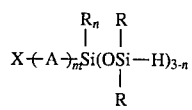

wherein X is a group selected from the group consisting of acryloxy, methacryloxy, and vinylphenyl, each R is independently selected from monovalent hydrocarbon groups free of aliphatic unsaturation, A is selected from a divalent hydrocarbon group having at least 2 carbon atoms or a group having the formula $-R_2-O-R^2-$ wherein $R^2$ is a divalent hydrocarbon group, m has an average value of 0 or 1, and n has an average value of 0, 1, to 2; and (B) an aliphatically unsaturated alicyclic epoxy compound having the general formula Z-Y wherein Z is a monovalent hydrocarbon group having an aliphatically unsaturated bond and Y is an alicyclic epoxy group, in the presence of:

(C) a hydrosilylation reaction catalyst.

10. A method according to claim 9, wherein the vinylphenyl group is selected from 4-vinylphenyl, 3-vinylphenyl, or 2-vinylphenyl.

11. A method according to claim 9, wherein X is a methacryloxy group.

12. A method according to claim 9, wherein R is selected from methyl or phenyl.

13. A method according to claim 9, wherein A is selected from ethylene, propylene, butylene, hexylene, or ethyleneoxypropylene.

14. A method according to claim 9, wherein Y is selected from 3,4-epoxycyclohexyl or 4-methyl-3,4-epoxycyclohexyl.

15. A method according to claim 9, wherein $R^2$ is selected from ethylene, propylene, butylene, or hexylene.

16. A method according to claim 9, wherein Z is selected from vinyl, allyl, butenyl, or hexenyl.

17. A method according to claim 9, wherein (C) is selected from chloroplatinic acid, alcohol solutions of chloroplatinic acid, platinum-olefin complexes, or platinum/vinylsiloxane complexes.

18. A method according to claim 9, wherein the mixture of step (I) further comprises a solvent.

19. A method according to claim 18, wherein the solvent is selected from benzene, toluene, xylene, hexane, heptane, tetrahydrofuran, diethyl ether, acetone, methyl ethyl ketone, ethyl acetate, butyl acetate, carbon tetrachloride, trichloroethane, chloroform, dimethylformamide, or dimethyl sulfoxide.

20. A method according to claim 18, wherein the solvent is hexane.

* * * * *